United States Patent
Latham et al.

(10) Patent No.: US 9,566,452 B2
(45) Date of Patent: Feb. 14, 2017

(54) SYSTEMS AND METHODS OF MODIFYING A PROTON BEAM IN A PROTON TREATMENT SYSTEM

(71) Applicant: ProNova Solutions, LLC, Knoxville, TN (US)

(72) Inventors: Stephen A. Latham, Sun Prairie, WI (US); Tyler Evors, Knoxville, TN (US); Joseph C. Matteo, Walland, TN (US); Jonathan Huber, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 0 days.

(21) Appl. No.: 14/492,379

(22) Filed: Sep. 22, 2014

(65) Prior Publication Data

US 2015/0083935 A1    Mar. 26, 2015

Related U.S. Application Data

(60) Provisional application No. 61/880,404, filed on Sep. 20, 2013.

(51) Int. Cl.
*A61N 5/10* (2006.01)
*G21K 5/04* (2006.01)

(52) U.S. Cl.
CPC ............... *A61N 5/1077* (2013.01); *G21K 5/04* (2013.01); *A61N 2005/1087* (2013.01); *A61N 2005/1095* (2013.01)

(58) Field of Classification Search
CPC ... A61N 5/10; A61N 2005/1087; H05H 15/00
USPC .... 250/492.3, 505.1; 315/500, 507; 600/436
See application file for complete search history.

(56) References Cited

U.S. PATENT DOCUMENTS

| | | |
|---|---|---|
| 7,053,389 B2 | 5/2006 | Yanagisawa et al. |
| 7,199,382 B2 | 4/2007 | Rigney et al. |
| 7,212,609 B2 | 5/2007 | Nagamine et al. |
| 8,003,964 B2 | 8/2011 | Stark et al. |

OTHER PUBLICATIONS

Patent Cooperation Treaty; Int'l Search Report; Form PCT/ISA/220 (Jul. 2014); Date of mailing: Dec. 15, 2014.

*Primary Examiner* — Jack Berman
(74) *Attorney, Agent, or Firm* — Pitts & Lake, P.C.

(57) ABSTRACT

Systems and methods of controlling characteristics of a proton beam emitted from a nozzle of a proton treatment system including one or more beam modifying members to define a characteristic of an emitted proton beam, and a clamping member mounted to the nozzle, the clamping member having one or more receiving portions to receive the one or more beam modifying members therein. In some embodiments, the beam modifying members comprise plate structures and the receiving portions include a plurality of slots spaced apart from one another on opposing surfaces of the clamping member to receive opposing ends of the plate structures.

18 Claims, 5 Drawing Sheets

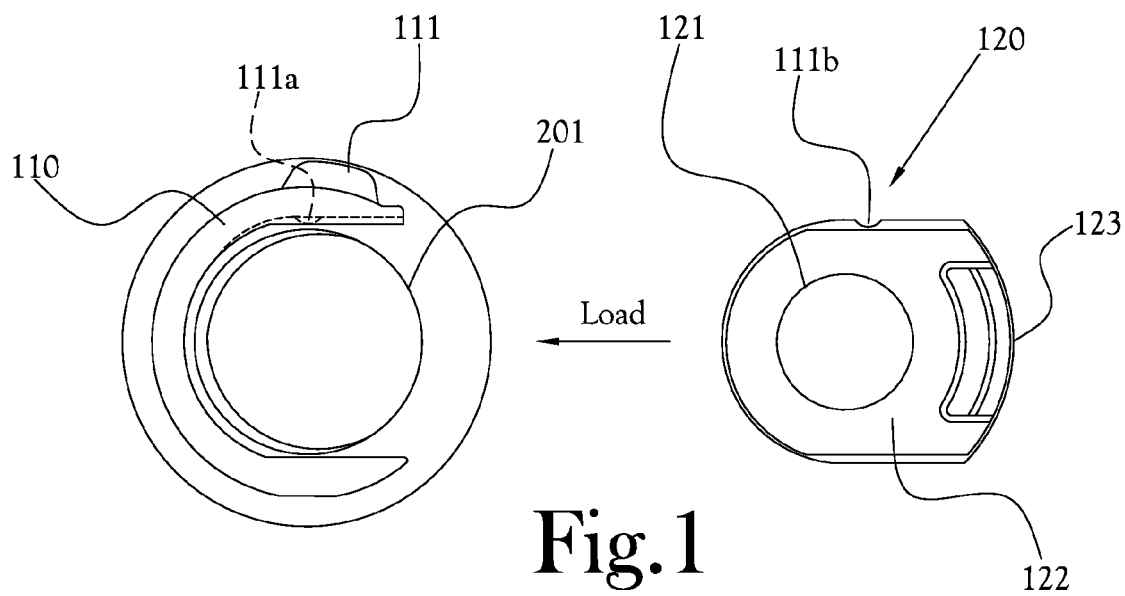
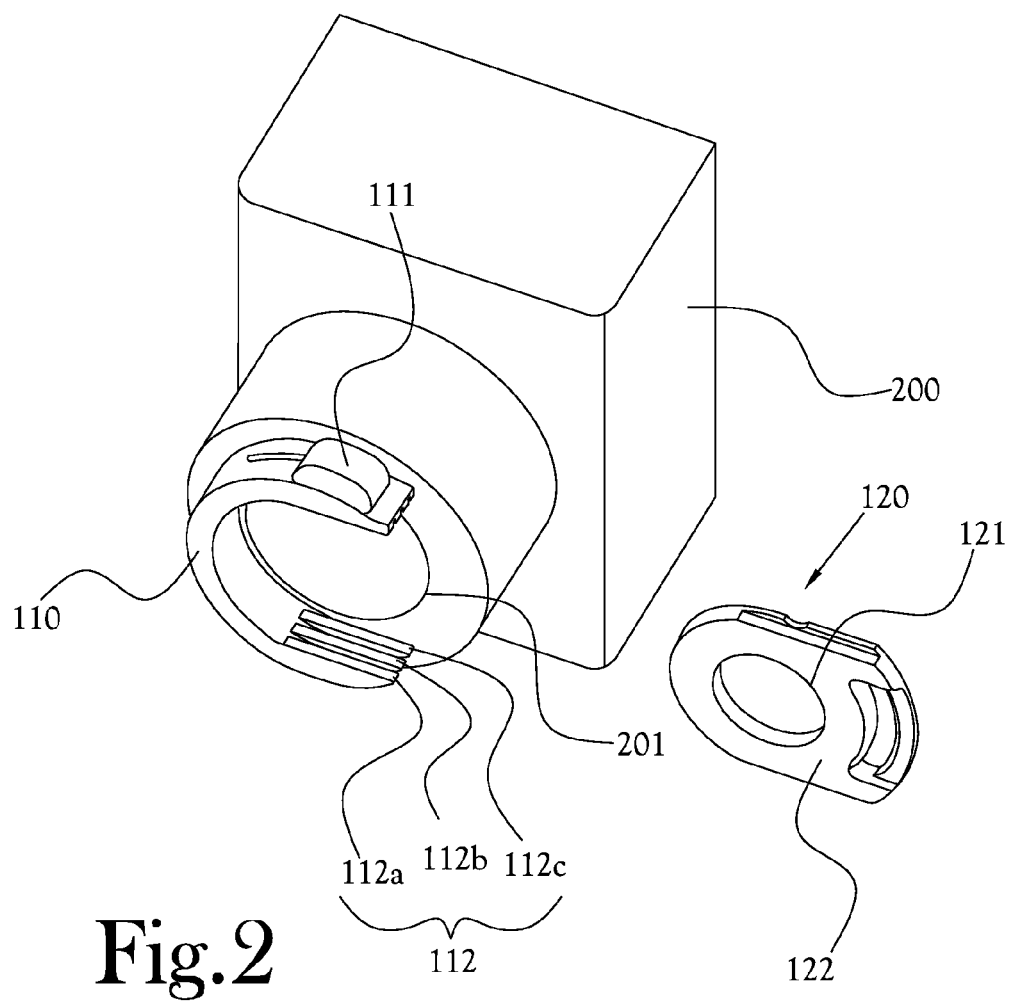
Fig.1
Fig.2

SYSTEMS AND METHODS OF MODIFYING A PROTON BEAM IN A PROTON TREATMENT SYSTEM

CROSS-REFERENCE TO RELATED APPLICATIONS

This application claims the benefit of U.S. Provisional Patent Application Ser. No. 61/880,404, filed on Sep. 20, 2013, the disclosure of which is incorporated herein in its entirety by reference.

FIELD OF INVENTION

The present general inventive concept relates to proton therapy for cancer treatment, and more particularly to a system to modify characteristics of a proton beam emitted from a proton treatment system.

BACKGROUND

Proton Therapy (PT) is a cancer treatment technology that uses high energy protons to penetrate a patient's body and deposit energy into treatment areas such as cancerous tumors. PT leverages the Bragg peak property of charged particles, such as protons, to deposit the majority of the particle's energy in the last few millimeters of travel, as opposed to conventional radiation therapy where the majority of energy is deposited in the first few millimeters of travel—which often causes significant damage to healthy tissue.

PT systems commonly implement a rotating gantry wheel to direct a beam of protons into the patient through a proton delivery nozzle from various positions around the patient during the course of treatment. The beam of protons directed into the patient is targeted into the three-dimensional shape of the desired treatment volume to deliver the therapeutic radiation precisely to the targeted location, while sparing the surrounding healthy tissue. A proton beam with a smaller cross sectional area provides greater precision in targeting, but requires more time and rotation of the gantry wheel than using a beam with a larger cross sectional area and clinicians must replace the snout of the PT system when changing between cross sectional areas.

The characteristics of the beam can include shape, size, cross-section, intensity, energy, etc. Thus, the characteristics of the proton beam include the cross-sectional shape and size of the proton beam, as defined by the aperture in the proton delivery nozzle. Traditional apertures are supported in place by a shielded snout that directs the flow of charged particles through the aperture. To shape or trim the beam of protons, the snout may include collimators to define and limit the spread of the proton beam, degraders to limit the intensity of the beam of protons, and compensators to affect the distance from the proton delivery nozzle that the charged particles deliver the majority of their energy. To change the aperture size or the trimming and focal properties of the proton beam in traditional proton nozzles, the entire snout assembly typically needs to be replaced, in addition to the clamp assembly, which can add time to the treatments using PT due to equipment change-outs. Further, because the snout contains radiation shielding, the snout is heavy and cannot be changed out without mechanical assistance.

BRIEF SUMMARY

Example embodiments of the present general inventive concept can be achieved by providing systems and methods that allow for the rapid modification of the nozzle aperture for various beam modifying effects without requiring a snout change. Example embodiments include a system to control characteristics of a proton beam emitted from a nozzle of a proton treatment system, including one or more beam modifying members to selectively define a characteristic of an emitted proton beam, and a clamping member mounted to the nozzle, the clamping member having one or more receiving portions to respectively receive the one or more beam modifying members therein.

Example embodiments of the present general inventive concept can also be achieved by providing a system to control characteristics of a proton beam emitted from a nozzle of a proton treatment system, including one or more beam modifying members to define a characteristic of an emitted proton beam, and a clamping member mounted to the nozzle, the clamping member having one or more receiving portions to receive the one or more beam modifying members therein.

The beam modifying members can be configured as a first set of plates, and the receiving portions can include a plurality of slots spaced apart from one another on opposing surfaces of the clamping member to receive opposing ends of each first plate.

The clamping members can include one or more detector units to detect the presence of a beam modifying member within the clamping member.

At least one of the beam modifying members can include a second clamping member having at least one receiving portion smaller than the receiving portions of the first clamping member to respectively receive one or more other beam modifying members therein.

One or more other beam modifying members can be configured as a second set of plates smaller than the first set plates, and the receiving portions of the second clamping member can include a plurality of slots spaced apart from one another on opposing surfaces of the second clamping member to receive opposing ends of each second plate.

The second clamping member can include one or more detector units to detect the presence of at least one beam modifying member within the second clamping member.

The clamping member can be disposed adjacent to a proton delivery nozzle aperture of the proton treatment system and downstream from the nozzle aperture.

The one or more and other beam modifying members can include one or more of a place-holder plate, aperture plate, collimator plate, compensator plate, degrader plate, or combinations thereof. The place-holder plate may not significantly modify the proton beam. The aperture plate may define a cross sectional area of the proton beam. The collimator plate may align the proton beam. The compensator plate may affect the Bragg peak distance of the proton beam. The degrader plate may reduce an intensity of the proton beam.

A plurality of beam modifying members can be stacked together side by side within the clamping member.

The one or more beam modifying members can include annular shielding.

The system may further include a compensator integrated with at least one beam modifying member.

The system may further include an output unit in communication with the one or more detector units to output presence information of a beam modifying member within the clamping member and/or second clamping member.

The one or more beam modifying members can include a handle portion to facilitate gripping of the beam modifying members by an operator of the proton treatment system.

The proton treatment system can include a snout, and the one or more beam modifying units can be interchanged in the clamping members without removing the snout from the proton treatment system.

Example embodiments of the present general inventive concept can also be achieved by providing a method of controlling characteristics of a proton beam emitted from a nozzle of a proton treatment system, including mounting a clamping member to a nozzle of a proton treatment system, the clamping member having one or more receiving portions provided therein, and interchangeably sliding one or more beam modifying members into a respective receiving portion, the one or more beam modifying members being selected to define a characteristic of a proton beam emitted from the nozzle, wherein the beam modifying members are configured as a first set of plates having a first size, and the receiving portions include a plurality of slots spaced apart from one another on opposing surfaces of the clamping member to receive opposing ends of each first plate, and wherein at least one of the beam modifying members includes a second clamping member having at least one receiving portion smaller than the receiving portions of the first clamping member to respectively receive one or more other beam modifying members therein.

The method may further include detecting the presence of at least one beam modifying member within the clamping members, and outputting presence information of the least one beam modifying unit to an output unit of the proton treatment system.

Additional features and embodiments of the present general inventive concept will be set forth in part in the following description and, in part, will be obvious from the description, or may be learned by practice of the present general inventive concept.

BRIEF DESCRIPTION OF THE DRAWINGS

The following example embodiments are representative of example techniques and structures designed to carry out objectives of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 1 is a frontal view of loading an aperture plate into a clamp;

FIG. 2 is an isometric view of a beam projector fitted with a clamp with an aperture plate, detailing the plate holders of the clamp;

DETAILED DESCRIPTION

Figure 3A:
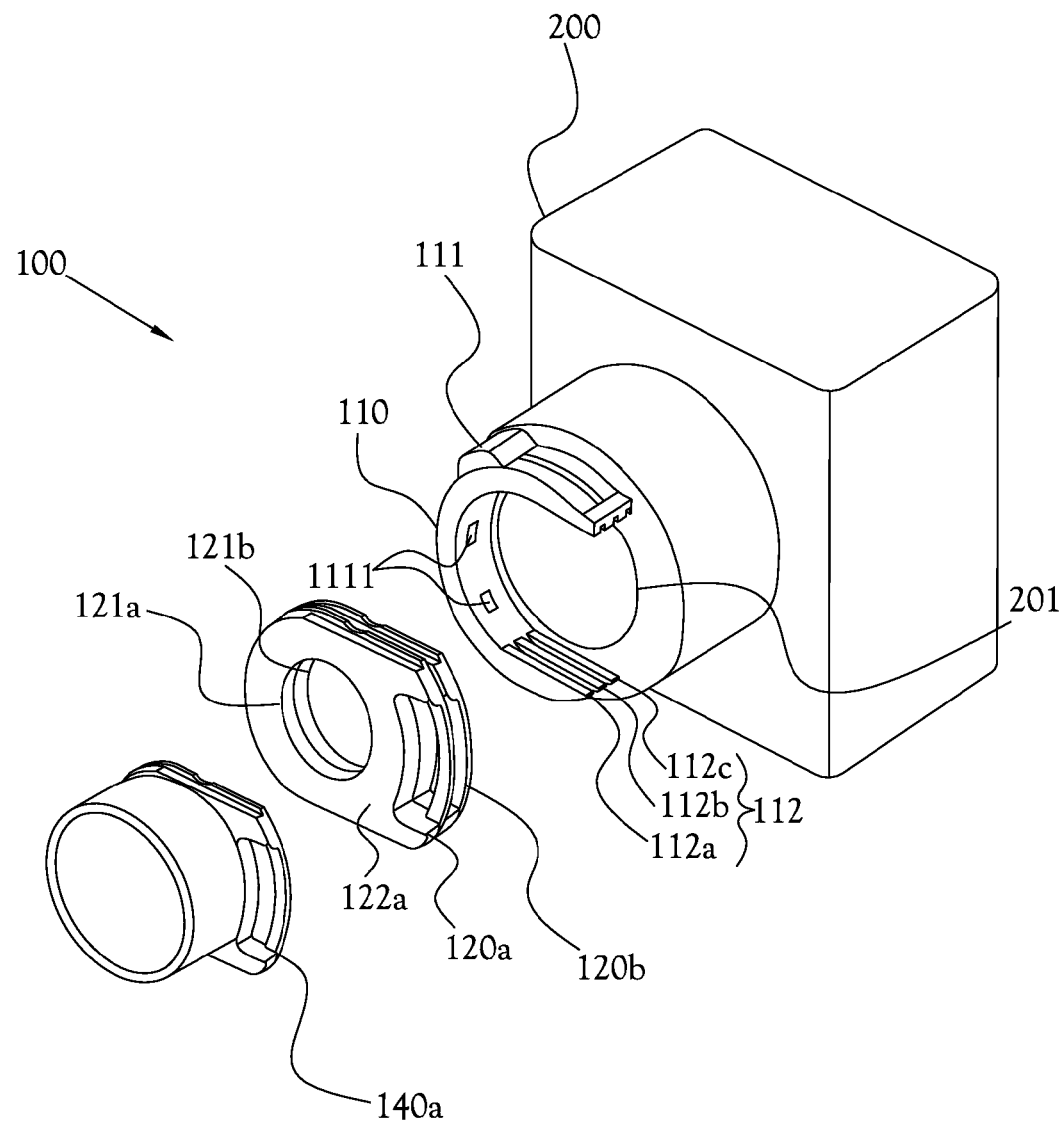
FIG. 3A is an exploded isometric view of one embodiment of an adaptive aperture clamp with a large field projection.

Reference will now be made to the following example embodiments of the present general inventive concept, examples of which are illustrated in the accompanying drawings. The example embodiments are described herein in order to explain the present general inventive concept by referring to the figures.

Example embodiments of the present general inventive concept enable a proton beam operator to quickly change a proton beam shape and size, for example, by selectively sliding multiple interchangeable beam modifying members, or plates, into a clamp mechanism for purposes of collimation, beam shaping, degrading, etc., without a time consuming snout change. Patients can receive large doses of radiation to the larger volumes of targeted locations and more precise doses of radiation to smaller volumes, particularly treatment from a direction having critical anatomic structures nearby the proton beam, of targeted locations, which can improve the efficacy and speed of treatment. It is noted that the term 'plate' may be used herein to refer to various components, but it is understood that the components are not limited to a plate-shape, or any particular shape. A variety of other shapes in addition to plate-shapes could be chosen with sound engineering judgment to configure the various components. The beam modifying members can be selectively installed by an operator of the proton therapy system, or they can be selected and installed by an automated system, such as a robot, based on a particular treatment plan.

FIG. 1 is a frontal view illustrating loading of an example embodiment beam modifying member such as aperture plate 120 into a clamp mechanism or clamping member 110 of the present general inventive concept. The aperture plate 120 defines an aperture 121 through which a beam of charged particles, such as a proton beam, is transmitted, with a shielded portion 122, which attenuates and/or reflects a portion of the beam that is not directed through the aperture 121. The aperture plate 120 can be slidably inserted into respective receiving portions of the clamp 110. In the illustrated example embodiment, the clamping member 110 is generally C-shaped with slots disposed on opposing surfaces of the clamp to receive one or more beam modifying members therein through one side. The beam modifying member, such as aperture plate 120, is in some embodiments shaped in the form of a plate to be received in a corresponding slot. In some embodiments, the clamping member 110 includes a locking element 111 to secure the aperture plate 120 to the clamping member 110 relative to the nozzle aperture 201. The locking member can take the shape of a protruding member 111a extending into the receiving slots of the clamping member 110 to secure and locate the beam modifying member via a mating receiving portion 111b, e.g., cutout, which receives the protruding member 111a. The protruding member can be spring loaded and/or lever driven such that the protruding member extends into the receiving portion to locate and/or drive the beam modifying member 120 into position as the beam modifying member is installed in the clamping member. The locking member can take a variety of configurations, such as a lever actuated sliding lock, spring loaded detent, etc., without departing from the broader spirit and scope of the present general inventive concept. Those skilled in the art will appreciate that although the embodiment of FIG. 1 illustrates a generally C-shaped clamp mechanism design, various clamp designs and shapes could be used, such as a slide-through design, a square-like shape, or other shape design, without departing from the scope and spirit of the present general inventive concept.

FIG. 2 is an isometric view of a beam projector fitted with a clamp 110 and aperture plate 120, detailing example plate holders 112 of the clamp. Referring to FIG. 2, the clamping member 110 includes plate holder 112, such as plate-slots 112a, 112b, 112c in which an aperture plate 120 or other plate types can be secured. The clamping member 110 illustrated in FIG. 2 is in some embodiments attached to a proton delivery nozzle 200 secured over a nozzle aperture 201. The lock 111 secures one or more aperture plates within plate-slots 112a-c. Plates secured in the plate-slots 112a-c can affect the beam or merely be place-holders for plates to occupy a plate-slot 112 without affecting the beam. Although the example embodiment of FIG. 2 illustrates three (3) plate-slots, more or less slots could be provided without departing from the broader scope and spirit of the present general inventive concept.

As described in further detail below, various types of plates can include, but are not limited to, aperture plates to trim the cross sectional area of the beam, beam collimator plates to collimate the particles in the beam, compensator plates to affect the Bragg peak effect's distance of majority energy delivery for particles in the beam, clamp plates to enable additional plates to affect the beam, and various combinations thereof. In particular, some example embodiments of the present general inventive concept include incorporating a precollimator as part of the apparatus holding a smaller sized aperture plate, providing for full radiation shielding of the patent with respect to the proton delivery nozzle.

Figure 3B:
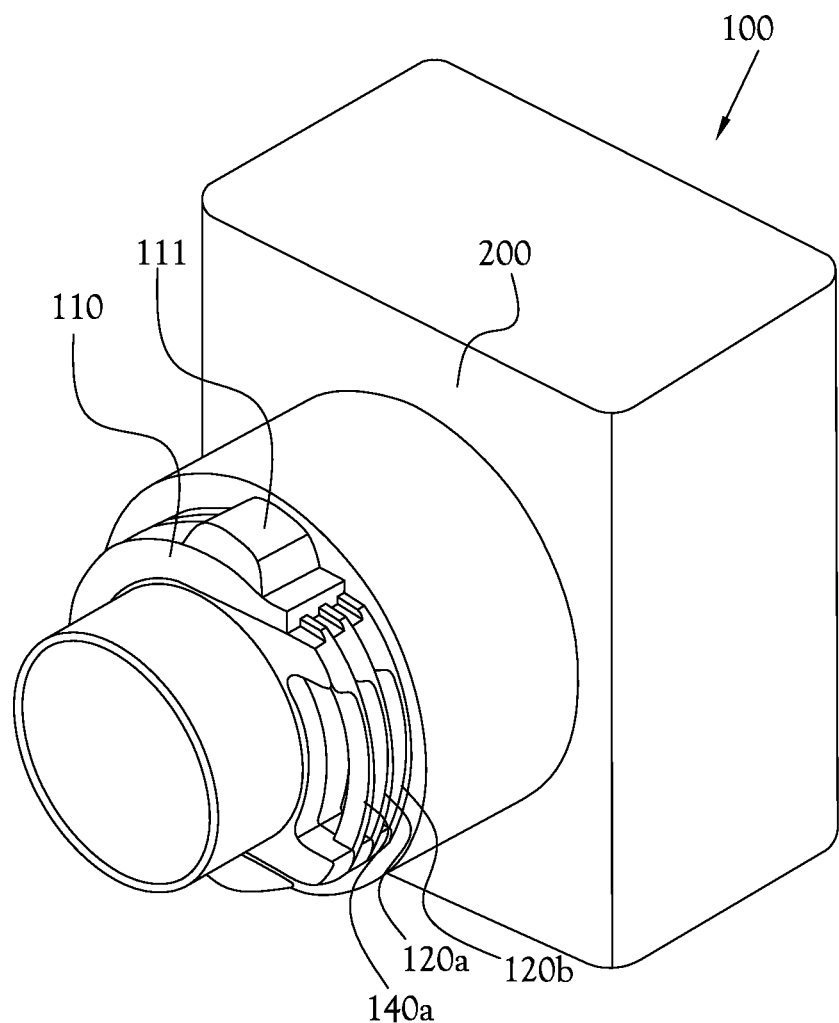
FIG. 3B is an isometric view of one embodiment of an adaptive aperture clamp with a large field projection.

FIGS. 3A and 3B illustrate an example embodiment of an adaptive aperture clamp 100 adapted for a large field projection. The illustrated embodiment uses two aperture plates 120a, 120b and a combination aperture/compensator plate 140a in its plate-slots 112. The aperture plates 120a, 120b define apertures 121a, 121b smaller in cross sectional area than the aperture 201 of the proton delivery nozzle 200, which trims the field size of the projected beam of charged particles. The two aperture plates 120a, 120b are seated in the clamp's plate-slots 112b, 112c proximal to the proton delivery nozzle 200 and a compensator plate 140a is placed in the distal plate-slot 112a. In this arrangement, the compensator plate 140a is downstream from the two aperture plates 120a, 120b and affects the Brag peak distance for charged particles in the beam.

Figure 4A:
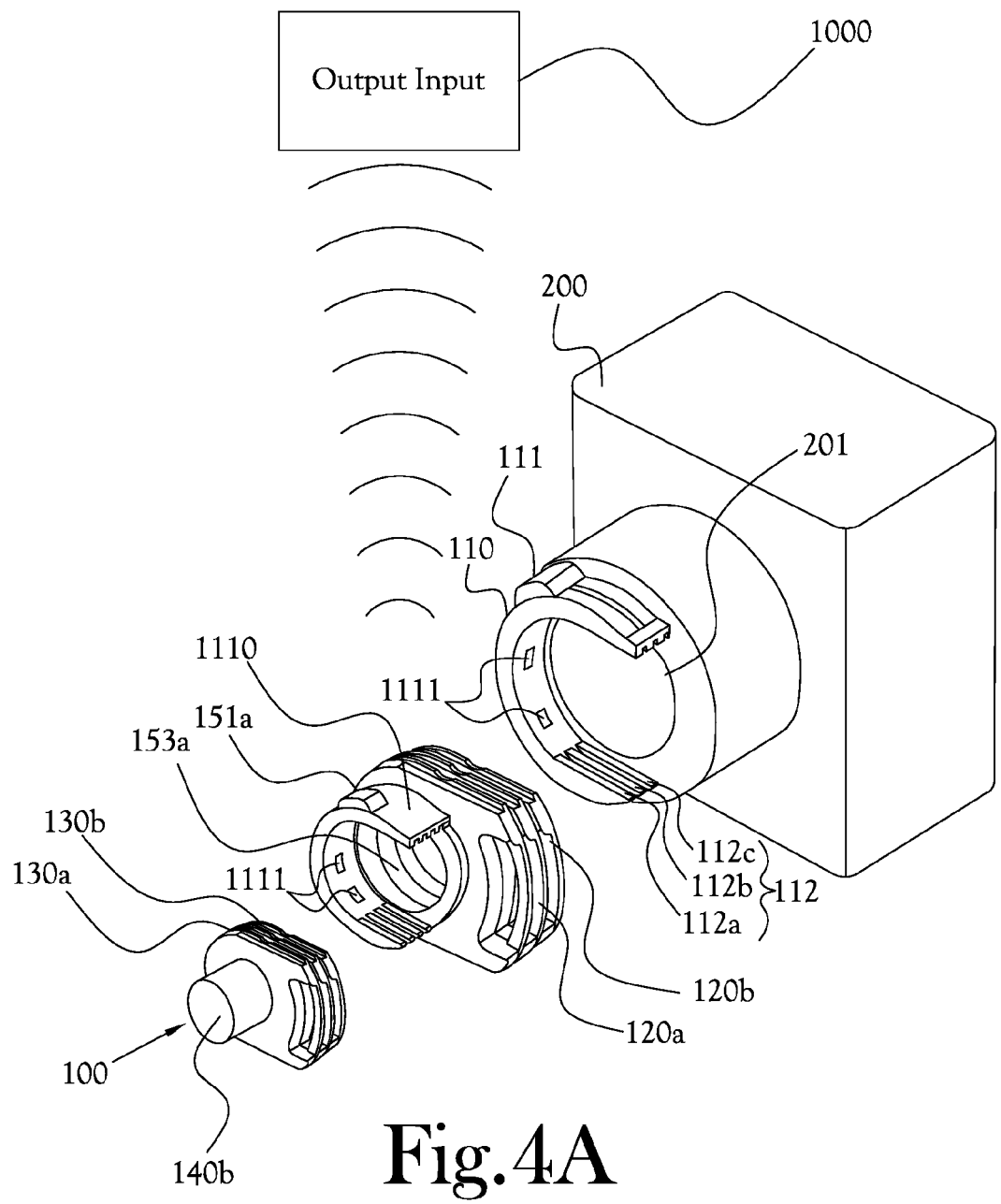
FIG. 4A is an exploded isometric view of one embodiment of an assembled adaptive aperture clamp with a small field projection.
Figure 4B:
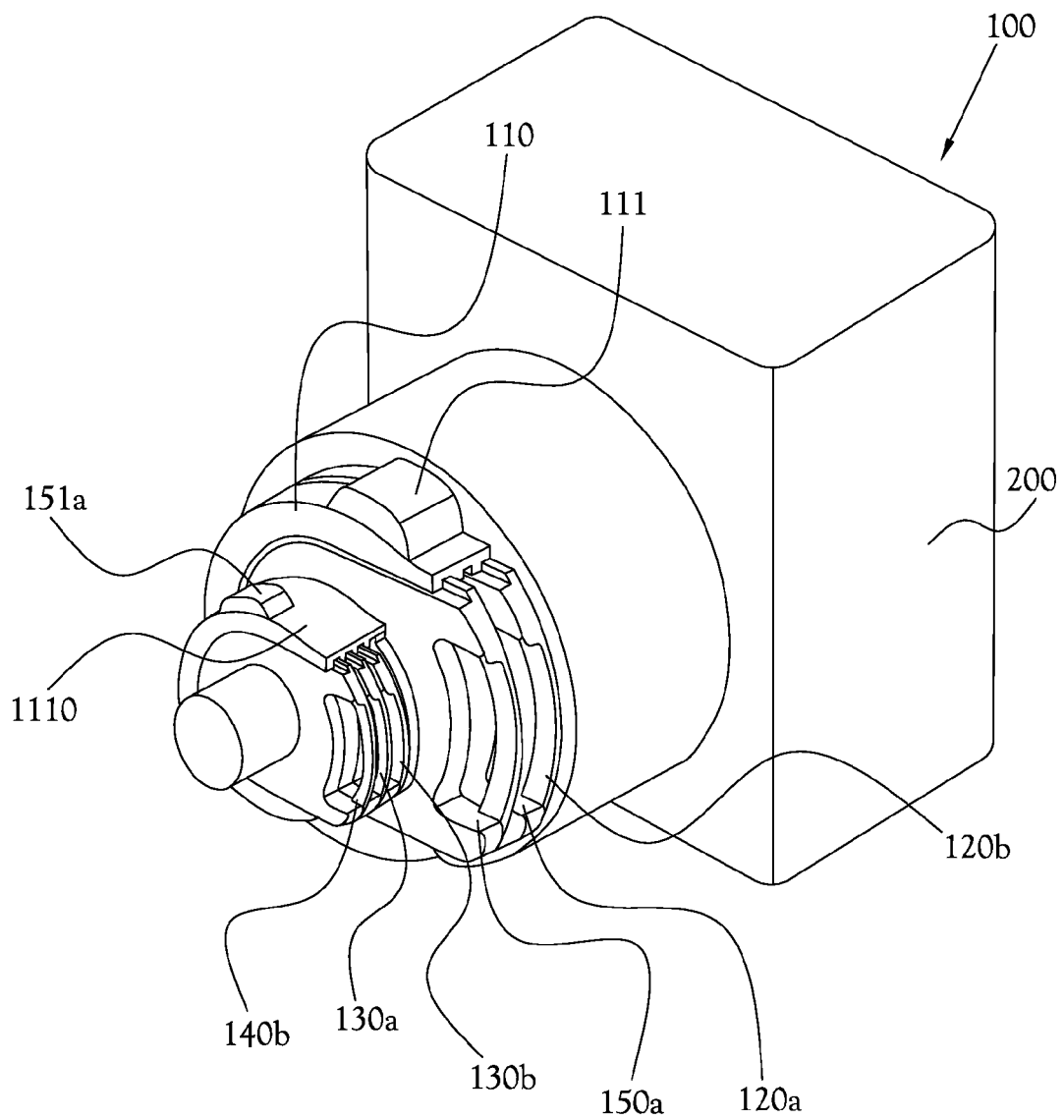
FIG. 4B is an isometric view of one embodiment of an assembled adaptive aperture clamp with a small field projection.

FIGS. 4A and 4B illustrate an example embodiment of an adaptive aperture clamp 100 adapted for a small field projection. The illustrated embodiment uses two aperture plates 120b, 120a, a clamp plate 150a, two collimator plates 130b, 130a, and a compensator plate 140b in its plate stack—arranged from upstream to downstream in this example. The illustrated embodiment builds on the embodiment of FIGS. 3A and 3B by adding a clamp plate 150a in place of the compensator plate 140a, enabling additional plates to be added to the plate stack to further define and affect the beam of charged particles by providing additional plate-slots 152. The clamp plate 150a has an aperture 153a substantially equal or larger in cross sectional area than the apertures 121a, 121b (FIG. 3A) of the upstream aperture plates 120a, 120b and has a lock 151a to secure plates into its clamp plate plate-slots 152a, 152b, 152c. In FIG. 4B, the precollimator plates 120a, 120b provide both a mechanism for mounting the patient collimators 130a, 130b and the additional, annular shielding required for full patient protection.

Referring to FIGS. 3A and 4A, the clamping member 110 can include one or more detection units 1111, such as switches or detectors, for detecting the presence of the aperture plates in the larger field size. The detection units can be actuated when the aperture plate(s) are installed in the clamping member 110. The detection units can be mechanical devices, electronic devices, optical devices, or other types of known or later developed detection units.

As illustrated in FIG. 4A, detector units 1111 can be installed in another clamping member 1110 of the precollimator plates 120a, 120b to detect the presence of aperture plates 130a, 130b in the smaller field size. Alternatively, the precollimator plates could carry detector mechanisms that are triggered directly by patient collimators 130a, 130b.

The detector units 1111 can be connected to an output unit 1000 to output presence and position information of the beam modifying members to monitor presence of patient apertures or other beam modifying members. The connection can be a wired or wireless electrical or optical connection, or other known or later developed connection method. The detector units can be used to confirm presence of an aperture or compensator plate within one or more clamping members. An array of detector units could be used to read a machined, binary code on the aperture plates and/or compensator plates. For example, four switches encoding four bits of digital information, or eight switches encoding eight bits, could be implemented, but the present general inventive concept is not limited thereto.

An option for integrating function is to integrate the aperture with compensator. The compensator material is a thermoplastic, typically acrylic or polyethylene. The aperture blank could be insert molded to the compensator blank. The the resulting composite blank would have the aperture and compensator sections machined in coordinated operations, then there would be one less device to be handled.

The apertures plates are typically quite heavy and can be difficult to handle. Handling can be improved by the addition of handling features. The figures show an aperture plate with a handle 123 integral to the material of the aperture, machined at the time a blank is made or machined at the time the final aperture is made. The handle portion can facilitate gripping of the aperture plates by an operator of the proton therapy system to enable the operator to quickly remove and/or install the plates into a respective clamping member, to change characteristics of the proton beam according to a particular treatment plan. Another option for adding a handle include adding additional holes during machining the aperture or blank with female-threaded holes to receive screw retaining a re-usable handle. The handle can be attached during use, removed and re-used on another aperture plate, keeping its cost relatively low. A handle which wraps all the way around the aperture can be used as an aperture carrier, i.e., another re-usable device which adds the ability to define locating features which may not be suited to the machined aperture itself.

While embodiments are described herein, it is not the intention of the applicant to restrict or in any way limit the scope of the appended claims to such detail. Additional modifications will readily appear to those skilled in the art. The general inventive concept in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A system to control characteristics of a proton beam emitted from a nozzle of a proton treatment system, comprising:
   a plurality of beam modifying members to define a characteristic of an emitted proton beam; and
   a clamping member configured to be mounted to the nozzle, the clamping member having a plurality of receiving portions disposed on the clamping member to respectively receive one of the plurality of beam modifying members therein, the plurality of receiving portions being configured to selectively and interchangeably receive multiple ones of the plurality of beam modifying members within the clamping member when the clamping member is mounted to the nozzle.

2. The system of claim 1, wherein the multiple ones of the beam modifying members are configured as a first set of plates having a first size, and the receiving portions include a plurality of slots spaced apart from one another on opposing surfaces of the clamping member to respectively receive opposing ends of each first plate.

3. The system of claim 2, wherein the clamping member includes one or more detector units to detect the presence of one or more of the beam modifying members within the clamping member.

4. The system of claim 1, wherein at least one of the beam modifying members includes a second clamping member having at least one receiving portion smaller than the receiving portions of the first clamping member to respectively receive one or more other beam modifying members therein.

5. The system of claim 4, wherein the one or more other beam modifying members are configured as a second set of plates smaller than the first set of plates, and the receiving portions of the second clamping member include a plurality of slots spaced apart from one another on opposing surfaces of the second clamping member to receive opposing ends of each second plate.

6. The system of claim 4, wherein the second clamping member includes one or more detector units to detect the presence of at least one beam modifying member within the second clamping member.

7. The system of claim 1, wherein the clamping member is configured to be mounted adjacent to a proton delivery nozzle aperture of the proton treatment system and downstream from the nozzle aperture.

8. The system of claim 1, wherein the plurality of beam modifying members include one or more of a place-holder plate, aperture plate, collimator plate, compensator plate, degrader plate, or combinations thereof, and wherein the place-holder plate is configured to not significantly modify the proton beam, the aperture plate is configured to define a cross sectional area of the proton beam, the collimator plate is configured to align the proton beam, the compensator plate is configured to affect a Bragg peak distance of the proton beam, and the degrader plate is configured to reduce an intensity of the proton beam.

9. The system of claim 1, wherein the multiple ones of the beam modifying members are stacked together side by side within the clamping member.

10. The system of claim 1 wherein the plurality of beam modifying members include annular shielding.

11. The system of claim 1, further comprising:
a compensator integrated with at least one beam modifying member.

12. The system of claim 3, further comprising:
an output unit in communication with the one or more detector units to output presence information of at least one of the beam modifying members within the clamping member.

13. The system of claim 6, further comprising:
an output unit in communication with the one or more detector units to output presence information of at least one of the beam modifying members within the clamping member.

14. The system of claim 1, wherein each of the plurality of beam modifying members include a handle portion to facilitate gripping of the beam modifying members by an operator of the proton treatment system.

15. The system of claim 5, wherein the proton treatment system includes a snout, and the plurality of beam modifying units can be interchanged in the clamping members without removing the snout from the proton treatment system.

16. The system of claim 1, further comprising a locking member to locate and secure the multiple ones of the beam modifying members within the clamping member relative to the nozzle, the locking member configured to cooperate with each of the plurality of receiving portions of the clamping member.

17. A method of controlling characteristics of a proton beam emitted from a nozzle of a proton treatment system, comprising:
mounting a clamping member to a nozzle of a proton treatment system, the clamping member configured to be mounted to the nozzle, the clamping member having a plurality of slotted receiving portions disposed on the clamping member to respectively receive one of the plurality of beam modifying members therein, the plurality of receiving portions being configured to selectively and interchangeably receive multiple ones of the plurality of beam modifying members within the clamping member when the clamping member is mounted to the nozzle; and
interchangeably sliding one or more of the plurality of beam modifying members into a respective receiving portion, the one or more beam modifying members being selected to define a characteristic of a proton beam emitted from the nozzle,
wherein the one or more beam modifying members are configured as a first set of plates having a first size, and the receiving portions include a plurality of slots spaced apart from one another on opposing surfaces of the clamping member to receive opposing ends of each first plate, and
wherein at least one of the beam modifying members includes a second clamping member having at least one receiving portion smaller than the receiving portions of the first clamping member to respectively receive one or more other beam modifying members therein.

18. The method of claim 17, further comprising:
detecting the presence of at least one beam modifying member within the clamping members; and
outputting presence information of the least one beam modifying unit to an output unit of the proton treatment system.

* * * * *